(12) United States Patent
Gao et al.

(10) Patent No.: US 11,679,123 B2
(45) Date of Patent: Jun. 20, 2023

(54) N-ACYLATED HYALURONIC ACID FOR HYPERURICEMIA AND GOUTY ARTHRITIS

(71) Applicants: Queen's University at Kingston, Kingston (CA); Jilin University, Changchun (CN)

(72) Inventors: Yin Gao, Jilin (CN); Tassos Anastassiades, Kingston (CA)

(73) Assignees: Queen's University at Kingston, Kingston (CA); Jilin University, Changchun (CN)

( * ) Notice: Subject to any disclaimer, the term of this patent is extended or adjusted under 35 U.S.C. 154(b) by 0 days.

(21) Appl. No.: 16/978,931

(22) PCT Filed: Mar. 7, 2019

(86) PCT No.: PCT/CA2019/050280
§ 371 (c)(1),
(2) Date: Sep. 8, 2020

(87) PCT Pub. No.: WO2019/169499
PCT Pub. Date: Sep. 12, 2019

(65) Prior Publication Data
US 2021/0000861 A1    Jan. 7, 2021

Related U.S. Application Data

(60) Provisional application No. 62/640,910, filed on Mar. 9, 2018.

(51) Int. Cl.
*A61K 31/728*  (2006.01)
*A61P 19/06*  (2006.01)
*A61P 37/06*  (2006.01)

(52) U.S. Cl.
CPC ............ *A61K 31/728* (2013.01); *A61P 19/06* (2018.01); *A61P 37/06* (2018.01)

(58) Field of Classification Search
CPC ......... A61K 31/728; A61P 19/06; A61P 37/06
See application file for complete search history.

(56) References Cited

U.S. PATENT DOCUMENTS

2014/0274941 A1* 9/2014 Anastassiades ...... A61K 31/728
514/54

FOREIGN PATENT DOCUMENTS

CA        2905610        9/2014

OTHER PUBLICATIONS

Chernos, M. et al "Rheological study of hyaluronic acid derivatives" Biomed. Eng. Lett., vol. 7, pp. 17-24. (Year: 2017).*
Babasola, O. et al "Chemically modified N-acylated hyaluronan . . ." J. Biol. Chem., vol. 289, No. 36, pp. 24779-24791. (Year: 2014).*
Ruoff, G. et al "Overview of serum uric acid treatment . . ." Postgrad. Med., vol. 128, issue 7, pp. 706-715. (Year: 2016).*
Mount, D. "The kidney in hyperuricemia and gout" Curr. Opin. Nephrol. Hypertens., vol. 22, No. 2, pp. 216-223. (Year: 2013).*
International Search Report and Written Opinion for corresponding International Application No. PCT/CA2019/050280 filed on Mar. 7, 2019.

* cited by examiner

*Primary Examiner* — Leigh C Maier
(74) *Attorney, Agent, or Firm* — Angela Lyon

(57) ABSTRACT

The invention provides a pharmaceutical composition of hyaluronic acid comprising repeating units of a disaccharide comprising glucuronic acid and N-acetylglucosamine, wherein a portion of the N-acetyl groups of the N-acetyl-glucosamine have been independently replaced with a group of the formula —N—C(O)—($C_2$-$C_4$)-alkyl for treating hyperuicemia and gouty arthritis. Studies show that this composition is promising as an anti-gout therapeutic agent, which combines both anti-inflammatory actions as well as anti uracemic effects.

18 Claims, 5 Drawing Sheets

C
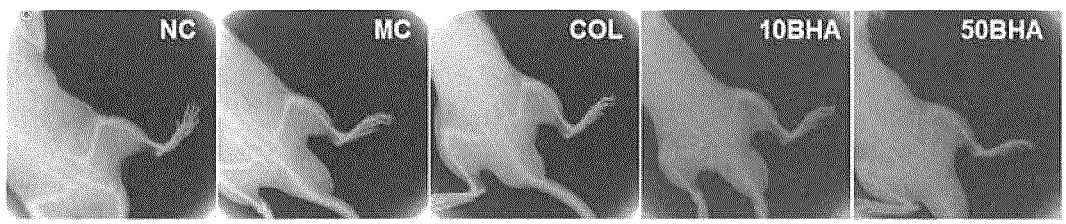
D
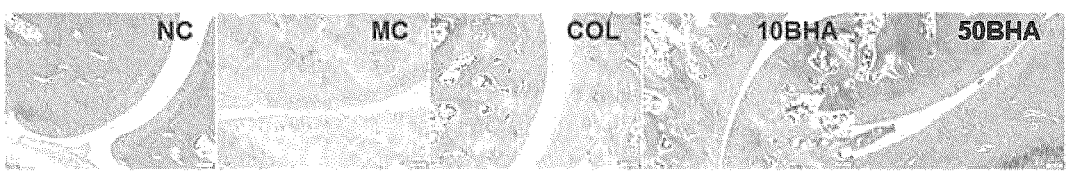
| E | NC | MC | COL | 10BHA | 50BHA |
|---|---|---|---|---|---|
| Day 1 | - | - | COL | - | - |
| Day 2 | - | - | COL | - | - |
| Day 3 | - | - | COL | - | - |
| Day 4 | - | - | COL | - | - |
| Day 5 | - | - | COL | - | - |
| Day 6 | Saline | MSU | MSU COL | MSU 10μg BHA | MSU 50μg BHA |
| Day 7 | - | - | COL | - | - |
| Day 8 | - | - | COL | - | - |
Fig. 2C-E

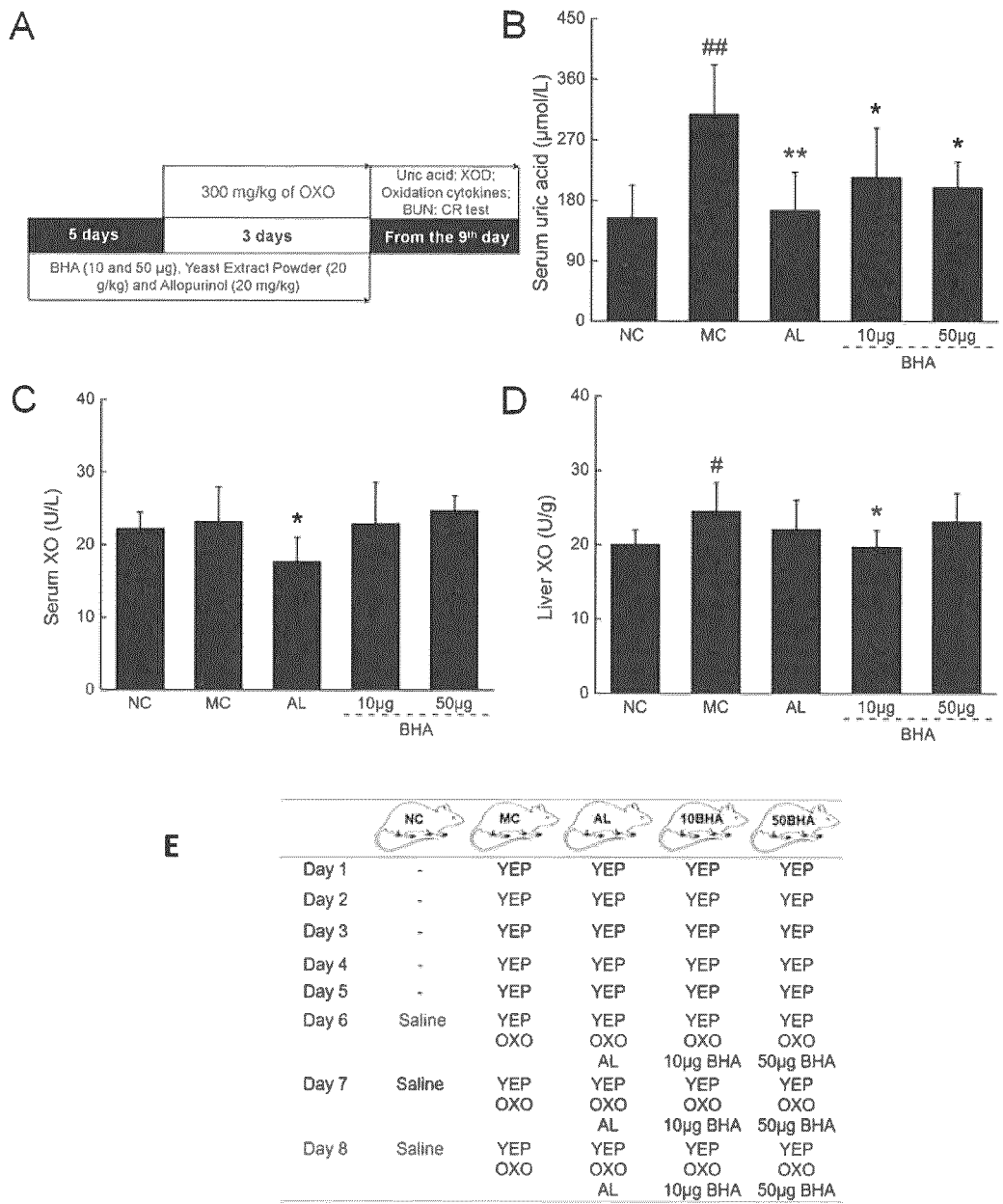
Fig. 3A-E

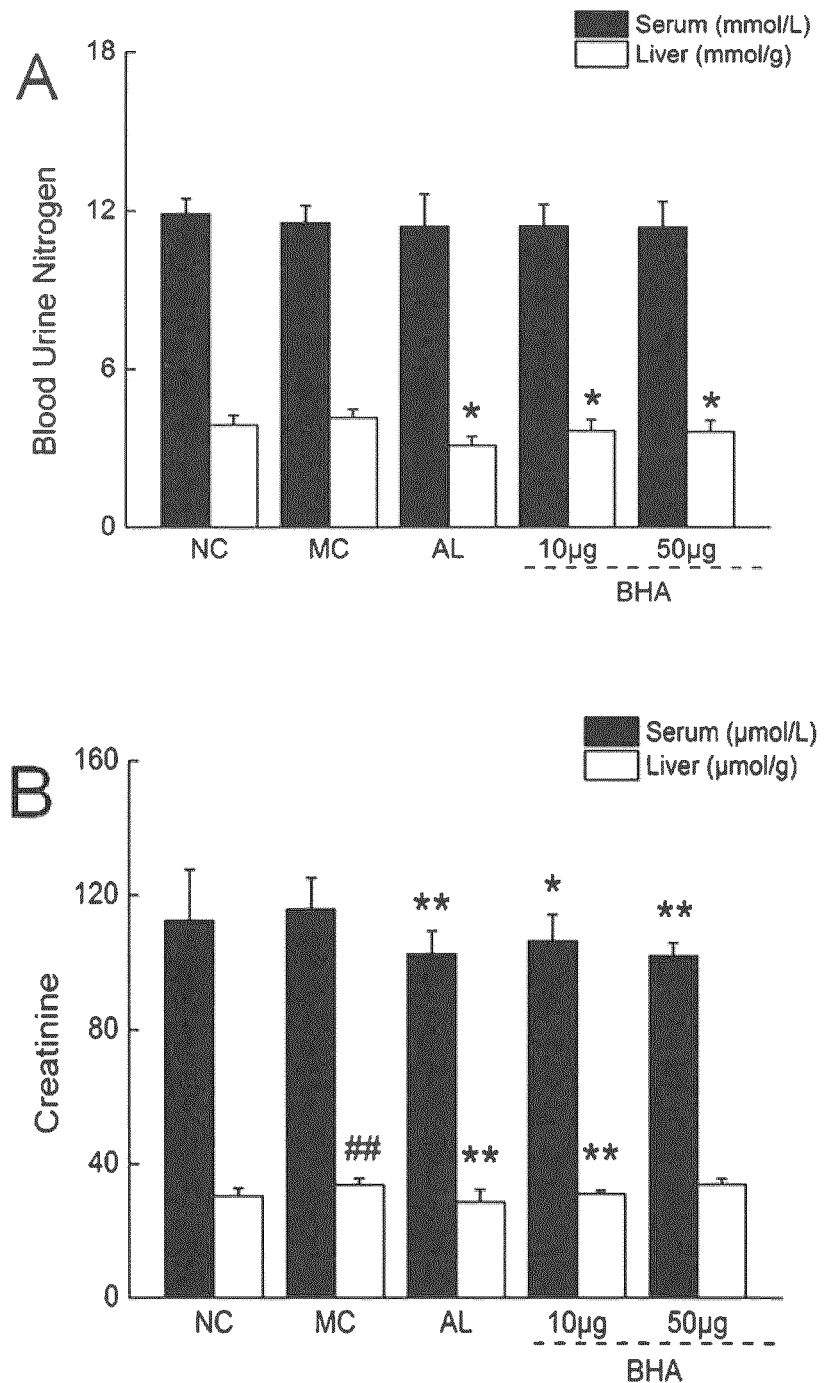
Fig. 4A-B

N-ACYLATED HYALURONIC ACID FOR HYPERURICEMIA AND GOUTY ARTHRITIS

FIELD

This disclosure relates to hyaluronic acid derivatives, and in particular, derivatives in which the N-acetyl group of hyaluronic acid has been substituted, and methods and uses thereof.

BACKGROUND

Hyaluronan (hyaluronic acid) is a widely distributed glycosaminoglycan in animal tissues, composed of alternating monosaccharide units of N-acetyl glucosamine (N-acetyl-2-amido glucose) and glucuronic acid. Hyaluronan has multiple functions including hydration, provision of matrix for cell migration and lubrication of joints. Intact hyaluronan has a high molecular mass of greater than 1,000 kDa but can exist in lower molecular mass forms, for example, 100-250 kDa. Intact hyaluronan is often derived commercially from rooster comb or from bacterial sources. High molecular mass hyaluronans have high viscosity, which is important in lubricant properties of joints. However, the size and likely folding of the greater than 1,000 kDa hyaluronans presents a different physico-chemical milieu to cell receptors and the organization of interacting matrix macromolecules, than the smaller molecular mass forms. The high molecular mass hyaluronan is believed to be degraded enzymatically to lower mass fragments in tissues.

Innate immunity in humans is mediated through Toll-like receptors or TLR. A constitutively active TLR4 mutant can induce NF-kappa B activation and thus increase the production of pro-inflammatory cytokines (Medzhitov, R. et al. (1997) *Nature* 388: 394). Recognition of bacterial lipopolysaccharide (LPS) by the innate immune system results in an inflammatory response characterized by the production of cytokines such as TNF, IL-1, IL-6, and IL-8; as well as gene activation of ICAM-1 (Lu Y. C. et al. *Cytokine*. (2008) 42:145-151). Hyaluronan can bind to a cell membrane receptor, CD44, and to a number of matrix proteins, notably the proteoglycan core protein link domain. CD44 has been reported to be up-regulated in some types of inflammatory arthritis, such as rheumatoid arthritis. Smaller molecular mass hyaluronans can interact with CD44 to activate cells that participate in inflammatory diseases and affect matrix molecules, which is generally not the case with high molecular mass hyaluronan (Horton MR. et al. *J Biol Chem* 1998 Vol. 273, No. 52, 35088-35094). A number of cytokines are induced and have higher levels in chronic inflammatory conditions. Humanized monoclonal antibodies to some of these cytokines are used therapeutically in chronic inflammatory conditions.

Gout is a metabolic and inflammatory syndrome associated with chronic hyperuricemia and characterized by monosodium urate (MSU) crystal deposition in joints and tissues. Lowering the serum level of uric acid, dissolving the MSU crystals and inhibiting the inflammatory reaction are considered as critical clinical tasks for the treatment of gout.

Gout is one of the most prevalent metabolic disorders that is accompanied by a high level of uric acid in the blood and monosodium urate (MSU) crystal precipitation in joints and tissues. Joint swelling and anaphylactic pain are the major symptoms of a gout attack. In the absence of treatment, an acute gouty attack can reoccur, causing severe pain and stiffness due to progressive joint tissue and bone deterioration. Uric acid crystals can also accumulate in tissues resulting in tophaceous gout, as a result of sustained hyperuracemia. Moreover, gout can potentially lead to a cytokine overproduction, systemic clotting, organ failure and death.

A primary pathogenetic mechanism of gouty arthritis is that monocytes uptake MSU crystals via endocytosis, and promote the secretion of inflammatory factors such as interleukins-1β (IL-1β) and tumor necrosis factor-α (TNF-α), which will then cause an influx of inflammatory cells and strengthen the inflammatory reaction. Inflammatory cytokines such as IL-1β and IL-8 are important factors in the pathogenesis of gouty arthritis, and thus inhibiting their production may constitute a strategy for managing difficult cases (So, A. et al. *Arthritis Res. Ther.* (2007) 9(2): 1-6; Busso, N. et al., *Arthritis Res. Ther.* (2010) 12(2):1-8; Kienhorst, L. B. E. et al., *Arthritis Rheumatol.* (2015) 67(12):3303-3313. IL-1β is an important inflammatory factor in the pathogenesis of gouty arthritis, and thus inhibiting its production is widely considered as an effective means to achieve anti-gout efficacy. Researchers also believe that anti-inflammatory factor interleukin-10 (IL-10) plays an important role in gout treatment. In addition, hyperuricemia is generally agreed to have a close relationship with gout, thus uric acid (UA) metabolism also plays a critical role in the pathology. The up regulation of xanthine oxidase (XO) which directly catalyzes the production of UA and lack of urate oxidase which is essential for UA metabolism can lead to hyperuricemia. There are a large number of reactive oxygen species (ROS) products that are generated along with UA production, which will promote oxidative stress, disrupting the biological redox equilibrium in vivo and ultimately damaging cellular functions. Hyperuricemia is often asymptomatic, but the probability of gout increases with elevated serum UA level. At present, alleviating pain, diminishing inflammation, relieving joint swelling and lowering the level of serum UA are the fundamental clinical objectives of gout therapy.

According to the pathology of gout, different drugs for treating gout are generally designed to deal with each of these tasks. Gout treatment drugs are mainly divided into anti-acute attack drugs and UA-lowering drugs. Anti-acute attack drugs primarily include colchicine (COL) and nonsteroidal anti-inflammatory drugs (NSAIDs). COL, an alkaloid from *Colchicum autumnale*, is mainly used to treat acute gout by reducing the inflammation and the deposition of UA crystals. Most NSAIDs act as nonselective inhibitors of cyclooxygenase to exert their anti-inflammatory and analgesic effects. However, the use of COL and NSAIDs may cause gastrointestinal discomfort, diarrhoea, and increase the risk of heart disease as well as other side effects. UA-lowering drugs include those that inhibit UA production (e.g., allopurinol and uricosuric drugs (e.g., probenecid). Serious side effects and single effect limit the use of allopurinol and probenecid. Therefore, the development of a comprehensive and safe alternative medication for gout treatment is urgently needed.

SUMMARY

In one aspect, the invention provides a pharmaceutical composition for preventing or treating hyperuricemia, gouty arthritis and/or tophaceous gout, comprising a pharmaceutically acceptable excipient or carrier, and a therapeutically effective amount of a hyaluronic acid derivative comprising repeating units of a disaccharide of Formula (I), wherein a portion of the disaccharide units of Formula (I) have been independently replaced with a disaccharide structure of Formula (II) wherein R is —C(O)—(C$_2$-C$_4$)-alkyl, or a pharmaceutically acceptable sodium- or potassium-salt, ester, or glucoside thereof,

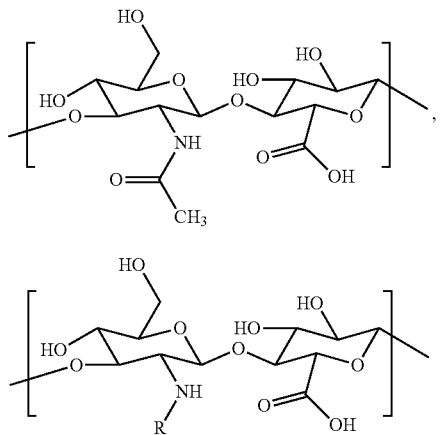

wherein the hyaluronic acid derivative has a molecular weight of at least about 20 kDa. In one embodiment, the hyaluronic acid derivative is cross-linked. In one embodiment of the pharmaceutical composition, R is —C(O)—(C$_3$)-alkyl. In one embodiment, the portion of N-acetyl groups which are replaced is at least about 10%. In one embodiment, the portion of N-acetyl groups which are replaced is between about 20% to about 80%. In one embodiment, the molecular weight is at least about 30 kDa. In one embodiment, the molecular weight is between about 20 kDa to about 250 kDa.

In one aspect the invention provides a method for preventing or treating of a condition or disease selected from the group consisting of hyperuricemia, gouty arthritis, tophaceous gout, gout, gouty inflammation, nephropathy, liver disease, liver damage, or nonalcoholic fatty liver disease, uric acid induced pain, oxidative stress diseases, acute gout, uric acid nephropathy, uric acid renal stones, cardiovascular disease, kidney diseases, Duchenne Muscular Dystrophy, Lesch-Nyhan syndrome, psoriasis, tumor lysis syndrome, and urinary calculi, comprising administering to a patient in need thereof the hyaluronic acid derivative of the above aspect. In one embodiment, the inflammation results from the production of pro-inflammatory cytokines in the patient. In one embodiment, the hyaluronic acid derivative comprises repeating units of a disaccharide comprising glucuronic acid and N-acetylglucosamine, wherein a portion of the N-acetyl groups of the N-acetylglucosamine have been independently replaced with a group of the formula —N—C(O)—(C$_2$-C$_4$)-alkyl, and wherein the hyaluronic acid derivative has a molecular weight of at least about 20 kDa, or a pharmaceutically acceptable sodium or potassium salt, ester, or glucoside thereof.

In one aspect the invention provides a method of modulating of creatinine levels, urea nitrogen, and/or uric acid levels, comprising administering to a patient in need thereof a hyaluronic acid derivative of the above aspect. In one embodiment, the modulating prevents rejection of a donor organ. In one aspect the invention provides use of a hyaluronic acid derivative in the manufacture of a formulation for the treatment of a condition or disease selected from the group consisting of hyperuricemia, gouty arthritis, tophaceous gout, gout, gouty inflammation, nephropathy, liver disease, liver damage, or nonalcoholic fatty liver disease, uric acid induced pain, oxidative stress diseases, acute gout, uric acid nephropathy, uric acid renal stones, cardiovascular disease, kidney diseases, Duchenne Muscular Dystrophy, Lesch-Nyhan syndrome, psoriasis, tumor lysis syndrome, and urinary calculi. In one embodiment, the inflammation results from the production of pro-inflammatory cytokines in the patient.

In another aspect the invention provides a method for modulating creatinine levels, BUN (blood urea nitrogen), and/or uric acid levels, comprising administering to a patient in need thereof a hyaluronic acid comprising repeating units of a disaccharide comprising glucuronic acid and N-acetylglucosamine, wherein a portion of the N-acetyl groups of the N-acetylglucosamine have been independently replaced with a group of the formula —N—C(O)—(C$_2$-C$_4$)-alkyl, and wherein the hyaluronic acid derivative has a molecular weight of at least about 20 kDa, or a pharmaceutically acceptable sodium or potassium salt, ester, or glucoside thereof.

In another aspect, the invention provides a method of preventing a) hyperuricemia, b) gouty arthritis, c) tophaceous gout, d) gout (e.g., acute or chronic), e) gouty inflammation, f) nephropathy, liver disease, liver damage, or nonalcoholic fatty liver disease, g) uric acid induced pain, h) oxidative stress diseases, i) acute gout, j) uric acid nephropathy, and/or k) uric acid renal stones.

In one aspect, the invention provides a method of treating hyperuricemia, which is a risk factors for certain diseases. In one aspect, the invention provides a method of increased xanthine oxidase activity or expression, which is a risk factors for certain diseases. In one aspect the invention provides a method for the treatment of cardiovascular diseases including atherosclerosis, metabolic syndrome; coronary heart disease, and/or heart failure. In one aspect the invention provides a method for the treatment of kidney diseases including acute kidney disease or chronic kidney disease. In one aspect the invention provides a method for the treatment of Duchenne Muscular Dystrophy, Lesch-Nyhan syndrome, psoriasis, tumor lysis syndrome and/or urinary calculi.

BRIEF DESCRIPTION OF THE DRAWINGS

For a better understanding of the invention and to show more clearly how it may be carried into effect, reference will be made by way of example to the accompanying drawings, which illustrate aspects and features according to embodiments of the invention, and in which:

FIG. 2C shows X-ray films of the right ankle bones of various rats.

FIG. 2D shows images of histopathological assessment of ankle joints in rats via H&E staining observing via observation microscopy (200×) wherein inflammatory cells were noted in the ankles of MSU crystals-injected rats (MC).

FIG. 2E shows a summary of treatment.

FIG. 3A shows a protocol summary and drug administration in hyperuricemic mice described herein.

FIG. 3B shows a bar graph displaying effects of AL and BHA on serum levels of UA in hyperuricemic mice.

FIG. 3C shows a bar graph displaying effects of AL and BHA on the XO levels in serum of hyperuricemic mice. Data are expressed as mean±S.D. (n=10) and were analyzed via a one-way ANOVA test followed by post-hoc Dunn's multiple comparison tests. #P<0.05 and ##P<0.01 versus normal control, * P<0.05 and ** P<0.01 versus model control.

FIG. 3D shows a bar graph displaying effects of AL and BHA on the XO levels in liver of hyperuricemic mice. Data are expressed as mean±S.D. (n=10) and were analyzed via a one-way ANOVA test followed by post-hoc Dunn's multiple comparison tests. #P<0.05 and ##P<0.01 versus normal control, * P<0.05 and ** P<0.01 versus model control.

FIG. 3E shows a summary of treatment.

FIG. 4A shows effects of AL and BHA on the serum and liver levels of urine nitrogen in hyperuricemic mice.

FIG. 4B shows effects of AL and BHA on the serum and liver levels of Cr in hyperuricemic mice.

DETAILED DESCRIPTION

Definitions

Figure 1:
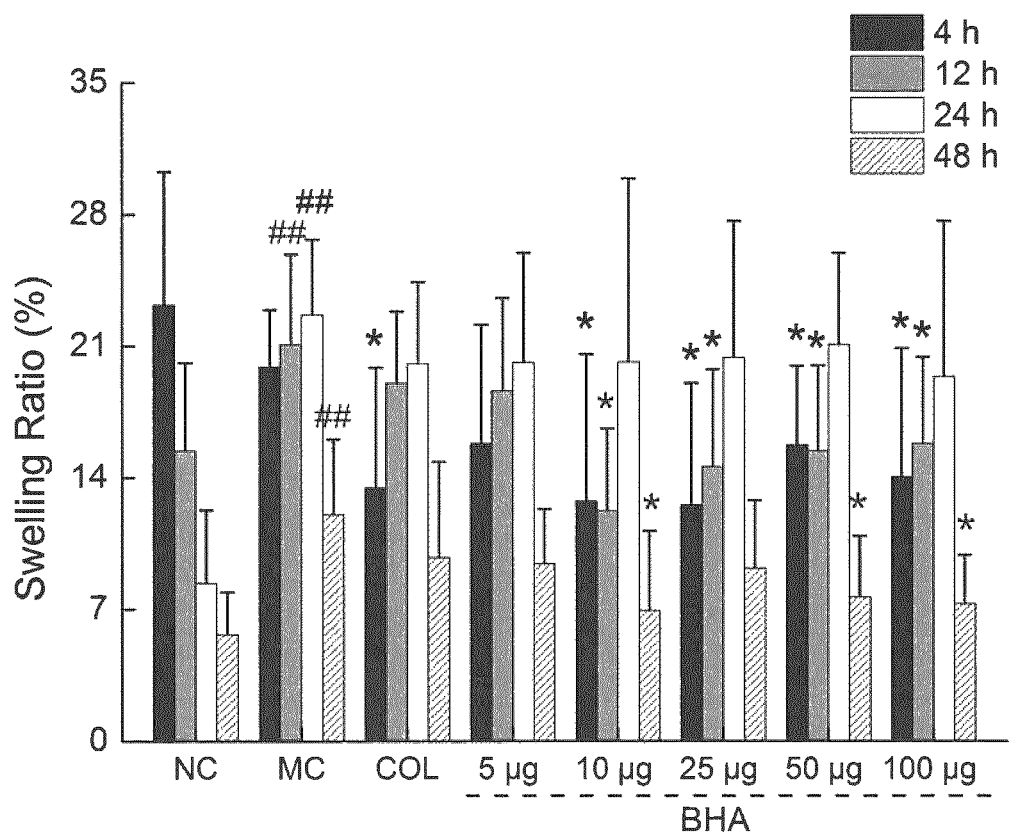
FIG. 1 shows a bar graph of swelling ratio versus treatment, for the ankle swelling rate in MSU crystals-injected rats. Data are expressed as mean±S.D. (n=6) and analyzed using a one-way ANOVA followed by post-hoc Dunn's multiple comparisons test. ##P<0.01 versus control rats, * P<0.05 versus model rats.

As used herein, the term "HA" refers to hyaluronic acid.

As used herein, the term "BHA" refers to N-butyrylated HA.

As used herein, the term "MSU" refers to monosodium urate.

As used herein, the term "ROS" refers to reactive oxygen species.

As used herein, the term "MDA" refers to malondialdehyde.

As used herein, the term "SOD" refers to superoxide dismutase.

As used herein, the term "NSAID" refers to non-steroidal inflammatory drugs.

As used herein, the term "acute gout" refers to pain and inflammation that may affect only one joint or more than one joint.

As used herein, the term "chronic gout" refers to repeated episodes of pain and inflammation at one joint or more than one joint.

Hyaluronic acid (HA), also called hyaluronan, is a linear polysaccharide belonging to the glycoamioglycan family, which is composed of simple repeating disaccharide units of N-acetyl-D-glucosamine (GlcNAc) and D-glucuronic acid (GlcA) with alternating β1,4 and β1,3 glycosidic linkages. The high molecular weight HA (HMHA) (>2000 kDa) is the main component of the extracellular matrix (ECM) and is abundant in human articular cartilage. While in the inflammatory conditions such as gouty arthritis, HMHA in the joint is degraded into lower molecular mass HA (LMHA) which binds to certain cell surface receptors such as toll-like receptors (TLRs) to stimulate overproduction of pro-inflammatory cytokines and facilitate removal of MSU by leukocyte, thus intensifying inflammation in the joint.

A previous study had shown that chemically N-butyrylated HA (BHA), of reduced molecular weight decreased production of pro-inflammatory cytokines significantly such as the THP-1 IL-1, IL-6, IL-8, and TNF-α in the stimulated human cultured macrophages (see International Patent Application No. PCT/CA2014/000225, published as WO 2014/138897, and Babasola O., et al. *J Biol Chem* 2014; 289:24779-91). This anti-inflammatory activity was through the interaction with the cell surface TLR-4 receptor and not through the TLR-2 receptor.

EMBODIMENTS

As described in detail herein, it was examined whether a chemically modified HA (specifically BHA) provided anti-inflammatory effect and alleviation of joint swelling in rats exhibiting MSU crystal-induced acute gout. The anti-hyperuricemia effects of BHA were also explored in mice exhibiting hyperuricemia that was induced by oteracil potassium (OXO) and yeast extract powder. The underlying mechanisms related to oxidative stress and inflammation were also investigated.

Hyaluronic acid (HA) has been used therapeutically, usually intra-articularly in osteoarthritis, to reduce the symptoms of knee pain. However, there is limited research on HA for the treatment of gout.

One aspect of the invention provides a pharmaceutical composition for treating hyperuricemia and gouty arthritis, including a pharmaceutically acceptable excipient or carrier, and a therapeutically effective amount of a hyaluronic acid derivative comprising repeating units of a disaccharide of Formula (I), wherein a portion of the disaccharide units of Formula (I) have been independently replaced with a disaccharide structure of Formula (II) wherein R is —C(O)—$(C_2$-$C_4)$-alkyl, or a pharmaceutically acceptable sodium- or potassium-salt, ester, or glucoside thereof,

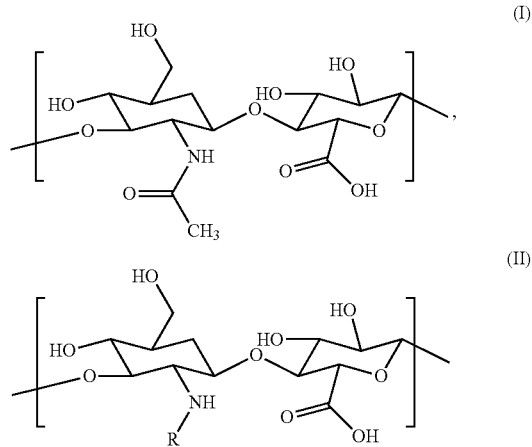

wherein the hyaluronic acid derivative has a molecular weight of at least about 20 kDa.

Embodiments provide methods for treating hyperuricemia, gouty arthritis, tophaceous gout, gout, gouty inflammation, nephropathy, liver disease, liver damage, or nonalcoholic fatty liver disease, uric acid induced pain, and/or oxidative stress diseases, including administering to a patient in need thereof a hyaluronic acid comprising repeating units of a disaccharide comprising glucuronic acid and N-acetylglucosamine, wherein a portion of the N-acetyl groups of the N-acetylglucosamine have been independently replaced with a group of the formula —N—C(O)—$(C_2$-$C_4)$-alkyl, and wherein the hyaluronic acid derivative has a molecular weight of at least about 20 kDa, or a pharmaceutically acceptable sodium or potassium salt, ester, or glucoside thereof.

As described herein, a MSU-induced gouty arthritis rat model and an oteracil potassium- and yeast extract-induced hyperuricemia mouse model were established. Partially butylated HA (see Formulas I and II above, wherein R is —C(O)—(C$_3$)-alkyl) was synthesized as a representative example of a compound of Formulas I and II above wherein R is —C(O)—(C$_2$-C$_4$)-alkyl. Therapeutic effects of partially butylated HA (BHA) were investigated with the animal models described herein. The expression level of cytokines and levels of oxidative stress markers were analyzed by ELISA.

Results described herein demonstrate therapeutic effects and suggest molecular mechanisms of BHA of approximately 30 kDa for treating hyperuricemia and gouty arthritis. Results demonstrate that intra-articular injection of BHA improved symptoms of ankle swelling in a rat model exhibiting MSU-induced gouty arthritis. Histological studies (H&E staining) indicated that intra-articular injection of BHA decreased the number of inflammatory cells and preserved joint space in comparison with untreated rats with MSU-induced gouty arthritis. Histopathologically, the injection of MSU crystals caused pronounced inflammatory cell infiltration in the synovium compared to the normal controls. Treatment with COL and the low dose of BHA attenuated the inflammation reaction in terms of that fewer inflammatory cells were observed in the groups of COL and 10BHA. The higher dose BHA (50BHA) was not as effective as the 10BHA dose. Furthermore, BHA reduced expression of pro-inflammatory cytokines including interleukin-1 beta (IL-1 beta), interleukin-8 (IL-8), and IFN-$\gamma$, down regulated the expression of monocyte chemotactic protein 1 (MCP-1) and increased the expression of anti-inflammatory cytokine interleukin-10 (IL-10). In addition, intraperitoneal injection of BHA significantly decreased serum level of uric acid and liver xanthine oxidase (XO) activity in mice with oteracil potassium- and yeast extract-induced hyperuricemia.

In one embodiment, a dose range of BHA if recommended of about 0.3 mg to about 40 mg per human for intra-articular injection, about 3 to about 400 mg/human for intraperitoneal injection, or about 25 mg/day to about 5 g/day for oral administration. In one embodiment oral administration is recommended as the route of administration. Notably, a person of skill in the art of the invention knows how to convert doses between species (see Anoop, A. B., et al., (2016), J. Basic. Clin. Pharm. 7(2): 27-31). For example, a dose of 10 ug/rat at a rat weight of ~200 g converts to 0.3-0.4 mg/human for a 65 kg human.

Although not wishing to be bound by theory, the inventors suggest that mechanisms could proceed via regulation of factors related to oxidative stress, such as lowering the level of nitric oxide in liver tissue, and lowering the levels of oxidative stress markers, reactive oxygen species (ROS) and malondialdehyde (MDA) in the serum and liver as well as increasing the activity of superoxide dismutase (SOD) in the liver. Taken together, these findings suggest that BHA has efficacy as an anti-gout therapeutic agent, which combines both anti-inflammatory actions as well as anti-uracemic effects.

As a worldwide disease with a well-documented history, the number of gout cases continues to increase each year. The proliferation of gout seems not only from the increased number of cases associated with this disease, such as the use of diuretics, alcohol consumption, purine intake and gastric bypass surgery, but is also related to the lack of an effective drug having both anti-inflammatory and anti-hyperuricemia effects. It has been reported that treatment with HA has a similar swelling inhibition effect as glucocorticoids and NSAIDs during treatment of arthritis. However, there are no reports regarding the effect of HA on anti-hyperuricemia. As described herein, the effect exhibited by BHA in gouty arthritis rats and hyperuricemic mice has been evaluated.

Gout attacks are accompanied by the infiltration of neutrophile granulocyte, which produce a large amount of ROS and lead to cell damage, as well as the release of lysosomal enzymes and inflammatory factors. Results suggested that during the 48 h of acute gout attack induced by MSU injection did not cause the structural damage of ankle joints (FIG. 2C). Histopathological sections showed significant infiltration of inflammatory cells into the ankles of rats (FIG. 2D) and MSU injection significantly increased the levels of MCP-1 and 6-Keto-PGF1$\alpha$, and depressed the level of IL-10 in rats. Treatment of 0.3 mg/kg COL and BHA significantly reversed the pathology in MSU crystal-injected rats. Data are expressed as mean±S.D. (n=10) and were analyzed via a one-way ANOVA test followed by post-hoc Dunn's multiple comparison tests. ##P<0.01 versus control rats, * P<0.05 and ** P<0.01 versus model rats. Therefore, it is postulated that this rat model provides an accurate representation of acute gout. As was the case with COL, treatment with BHA had a significant effect in alleviating ankle joint swelling induced by MSU injection in rats. Treatment with COL and BHA both diminished the infiltration of inflammatory cells. BHA treatment significantly depressed the contents of IL-1$\beta$, IL-8, MCP-1 and IFN-$\gamma$, but enhanced the levels of IL-10 in the serum of acute gout rats (Table. 2).

As shown in Table 1, the levels of IL-1$\beta$, IL-8, MCP-1, IFN-$\gamma$ and IL-10 were elevated significantly in the serum of patients with acute gout attack. IL-1 is involved in cartilage breakdown in osteoarthritis. Inhibition of IL-8 expression by BHA may contribute to its anti-inflammatory role in gouty arthritis. As shown herein, a percentage change of IL-8 in gouty patients compared to healthy volunteers was 784.6%. IL-8 is an important chemokine, which has the effect of promoting the recruitment of inflammatory cells and increasing the production of oxidant stress mediators. MCP-1, also known as CCL2, has the ability to induce chemotaxis mononuclear cells and plays an important role in rheumatoid arthritis. IFN-$\gamma$ promotes the development of inflammation. In contrast, IL-10, an anti-inflammatory cytokine, plays an important role in the control of immune responses and inhibiting the activation of macrophages. Therefore, anti-acute gout activity of BHA was achieved by inhibiting the inflammatory factors, promoting the anti-inflammatory cytokine, and reducing the overall level of inflammation in the rats. It was reported previously that UA can interact with cell surface receptor TLR4 to activate the TLR4-NLRP3 inflammasome, leading to caspase-1-dependent cleavage of pro-IL-1$\beta$, thereby triggering the release of IL-1$\beta$. Thus, the mechanism of the anti-inflammatory effects of BHA was probably through binding of BHA to TLR4 to prevent TLR4 from interacting with UA, thus regulating the NF-$\kappa$B signaling pathway. In addition, the elevated concentration of IL-10 in the serum of gouty patients may be related to the feedback regulation.

In one study, a histopathological assessment was conducted of synovium in ankle joints of rats after H&E staining. The right ankles of mice were excised and fixed in 4% paraformaldehyde, and subsequently decalcified using 10% ethylenediaminetetraacetic acid. They were then dehydrated via processing in alcohol/xylene mixtures with different proportions and concentrations. The histological sections were stained with hematoxylin and eosin. The histopathological changes of the joint synovium were assessed for the degree of inflammatory cell infiltrate, by an experienced histopathologist. Microscopy at magnifications of 40×, 100×, 200× and 400× were investigated for typical areas for each of the five groups. Normal rats (NC), displayed normal synovium. Increased inflammatory cell infiltration was noted in the synovium of MSU crystal-injected rats (MC). Treatment with COL, and 10 µg of BHA partially prevented the pathological changes seen in the MSU crystal-injected rats.

The level of serum UA is considered to be a direct indicator of the clinical diagnosis of hyperuricemia, and XO is an enzyme that plays a key catalytic role in the process of UA production. Results suggest that the levels of serum UA and liver XO increased significantly in hyperuricemic mice. However, with the treatment of the XO inhibitor-AL, the serum UA levels were reduced to normal levels and serum XO activity was significantly inhibited in hyperuricemic mice. As was the case with AL, treatment with BHA significantly reduced the serum UA levels and administration with 10 µg BHA dramatically reduced liver XO activity while administration with 50 µg BHA did not significantly reduce XO activity beyond that obtained with 10 µg BHA. Notably, oral administration with AL resulted in reduction of the serum UA to normal levels and this was also the case with BHA, which significantly reduced the serum UA levels (FIG. 3B). The dose of 10 µg BHA intra-peritoneally dramatically reduced liver XO activity.

Therefore, BHA treatment showed potentials in treating gouty arthritis by acting as an anti-inflammatory agent. Anti-hyperuricemia activity of BHA was achieved at least partly by inhibiting the activity of XO and reducing the serum UA levels. Treatment with 50 µg BHA had no significant effect on XO activity in the livers of hyperuricemic mice, but significantly decreased the serum UA levels (see FIG. 3A-E). Therefore, it is clear that BHA treatment for hyperuricemia is not limited to inhibiting XO activity.

XO could catalyze the oxidation of hypoxanthine and xanthine c to UA, which would be accompanied by a large amount of oxygen free radicals. In hyperuricemic mice the levels of ROS and MDA were significantly elevated in the liver, and the content of SOD in the serum was significantly diminished. MDA was formed by the degradation of polyunsaturated fat by ROS, and thus could be considered a biomarker for oxidative damage. BHA treatment significantly decreased the levels of ROS in the serum and liver and increased the level of SOD in the liver of hyperuricemia mice, which is consistent with the observation of lowered serum UA level. It has been reported that hyperuricemia is closely related to renal dysfunction and UA plays a major role in this pathology. Cr and urea nitrogen could be used as indicators of renal function evaluations. Both the Cr and urea nitrogen were measured in serum and in liver to access pathogenenic change in this hyperuricemia mouse model as well as to evaluate the safety of BHA treatment. Hyperuricemic mice exhibited a level of liver Cr that was significantly increased while there was no substantial increase of serum Cr. As was the case with treatment of the hyperuricemia mice with AL, treatment with BHA significantly reduced the urea nitrogen in liver and Cr in the serum and liver. As discussed above, BHA treatment significantly reduces the level of ROS in hyperuricemic mice and thus could provide a protective effect on renal function as AL. In hyperuricemic mice the level of liver Cr increased significantly. As is the case with AL, treatment with BHA significantly reduced the BUN in liver and Cr in the serum and liver (see FIG. 4). From these results it can be seen that BHA treatment significantly reduces the level of oxidation in hyperuricemic mice and has a protective effect on renal function.

BHA has the effect of inhibiting ankle swelling and inflammatory reactions induced by MSU injection, and reducing the serum UA content in mice with hyperuricemia induced by OXO and yeast extract powder. BHA may exhibit anti-gout and anti-hyperuricemia effects via a primary mechanism involving the inhibiting of inflammatory factors (IL-1β, IL-8, MCP-1 and IFN-γ) and the promotion of the anti-inflammatory cytokine (IL-10) to reduce the level of inflammation in the rats and inhibit the XO activity by regulating oxidative stress in the mice. Meanwhile, BHA has a certain role in protecting the renal function of hyperuricemic mice. In conclusion, BHA is a candidate for clinical gout treatment due to its excellent pharmacological activity.

Figures 2A, 2B:
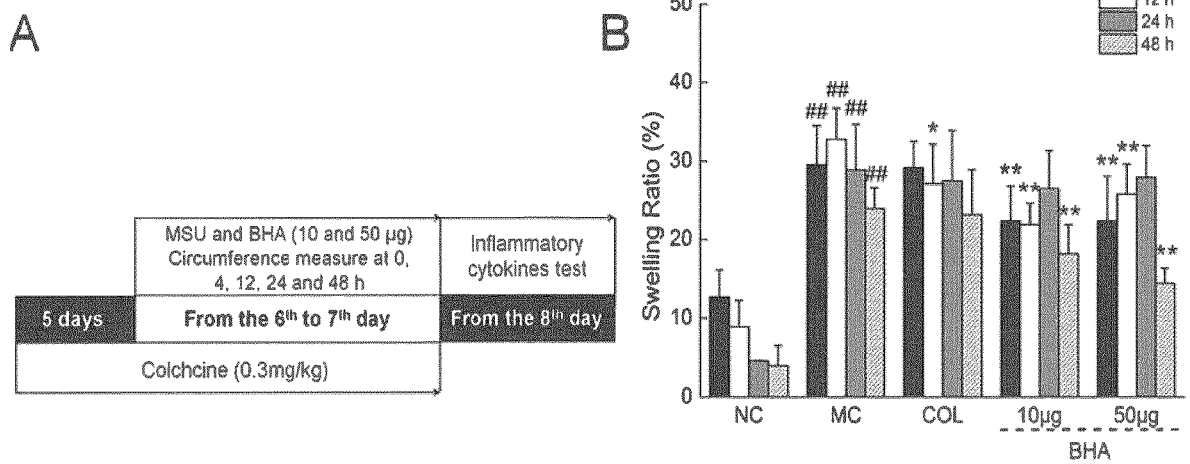
FIG. 2A shows a protocol summary of MSU crystal injection and drug administration in rats described herein.
FIG. 2B shows a bar graph of rate of ankle swelling versus treatment in MSU crystal-injected rats.

In regard to effects of BHA on rats that have acute gout induced by MSU crystals, MSU injection significantly increased the swelling ratios of the right ankles in rats (by 29.5%, 32.8%, 28.8% and 23.9% at 4, 12, 24 and 48 h after MSU injection, respectively, P<0.01, F=66.51 to 203.12; FIG. 2B compared with control rats. Treatment with 0.3 mg/kg COL suppressed ankle swelling at 12 h (P<0.05, F=6.307; FIG. 2B) compared to the MSU treated group. Treatment with BHA at the doses of 10 µg and 50 µg suppressed the ankle swelling of each rat at 4 h, 12 h and 48 h (P<0.01, F=9.06 to 68.75; FIG. 2B) in comparison with the MSU treated group. The 10 µg BHA treatment provided the best suppression of swelling at 12 h, and the swelling ratio was reduced by 11.0% (P<0.01, F=42.11; FIG. 2B). Additionally, 50 µg BHA treatment provided the best swelling suppression at 48 h, with a swelling ratio reduction of 9.5% (P<0.01, F=68.75; FIG. 2B). In addition, X-ray results showed that no injuries were visible in the ankle bones of all rats (see FIG. 2C). According to the pathology of gouty arthritis, the injection of MSU crystal caused an inflammatory cell infiltration in the gouty arthritis model group, which was not observed with the control group and the treatment groups. It is encouraging that COL and BHA treatment can improve this phenomenon (see FIGS. 2A-E).

The results show that fifteen inflammatory factors in gout were detected. In comparison to the control group, the contents of MCP-1 and 6-Keto-PGF1α were increased (P<0.05, F=5.25 to 14.97; Table 2), IL-10 decreased dramatically (P<0.05, F=5.27; Table 2), while IFN-γ and NF-κB were not significantly improved (P>0.05, F=1.08 to 4.52; Table 2) in the serum of MSU injection rats. Compared to rats injected with MSU, treatment with 0.3 mg/kg COL only decreased the level of MCP-1 by 9.93% (P<0.05, F=7.60; Table 2) in the serum, treatment with 10 µg BHA significantly decreased the level of IL-8 and MCP-1 by 7.13% and 7.76% (P<0.05, F=5.17 to 8.72; Table 2) and increased IL-10 by 9.49% (P<0.05, F=5.875; Table 2), while treatment with 50 µg BHA significantly decreased the level of IL-1β, IL-8, MCP-1 and IFN-γ by 5.56%, 6.55%, 15.58% and 33.18% (P<0.05, F=5.84 to 14.29; Table 2), respectively.

In regard to effects of BHA on hyperuricemia mice, elevated levels of serum UA are a symptom of hyperuricemia. In comparison with the normal mice, the levels of serum UA in hyperuricemia mice was enhanced significantly (P<0.01, F=19.99, see FIG. 3B). In the study with results presented in FIG. 3A-E, data are expressed as mean±S.D. (n=10) and were analyzed via a one-way ANOVA test followed by post-hoc Dunn's multiple comparison tests. #P<0.05 and ##P<0.01 versus normal control, * P<0.05 and ** P<0.01 versus model control. Treatment with BHA significantly suppressed serum UA levels (P<0.05, F=5.26 to 7.23; see FIG. 3B) in a similar manner as was exhibited by AL. Treatment with 20 mg/kg AL suppressed serum UA level by 46.38% (P<0.01, F=11.65; see FIG. 3B).

XO plays an important role in the production of UA and treatment of hyperuricemia. In mice with hyperuricemia, liver XO levels are intensified by 22.52% (P<0.05, F=7.36; FIG. 3D) compared to those observed in mice belonging to the control group. Compared to untreated mice, AL treatment reduced XO levels in the serum by 23.76% (P<0.05, F=8.17; FIG. 3C) and 10 μg BHA treatment reduced XO levels in the liver by 19.78% (P<0.05, F=7.80; FIG. 3D) only.

XO catalyzes the production of ROS during the synthesis of UA, which poses an elevated risk to renal function. In hyperuricemic mice, the levels of ROS, GSH-Px, CAT and MDA in the serum (P>0.05, F=0.43 to 1.79; Table 3) and the levels of SOD, GSH-Px and CAT in the liver (P>0.05, F=0.34 to 0.56; Table 3) exhibited no significant changes. However, the levels of ROS and MDA in the liver increased significantly (P<0.05, F=5.68 to 16.42; Table 3), while that of SOD in the serum decreased by 7.81% (P<0.05, F=6.72; Table 3). Treatment with AL suppressed the levels of ROS and MDA in the serum and liver by 9.48%, 17.86 and 6.66%, 13.47% (P<0.05, F=5.80 to 29.75; Table 3). The administration of 10 μg BHA strongly decreased the ROS levels in both the serum and liver by 14.87% and 8.04% (P<0.01, F=10.50 to 21.99; Table 3), respectively. Meanwhile, 50 μg BHA also significantly decreased the ROS levels both in the serum and liver by 14.63% and 9.59% (P<0.05, F=6.64 to 22.43; Table 3). Treatment with 10 and 50 μg BHA both significantly improved liver SOD by 12.77% and 13.69% (P<0.05, F=8.52 to 16.27; Table 3). In hyperuricemic mice, the levels of liver Cr increased significantly by 11.09% (P<0.01, F=10.95; FIG. 4B). Treatment with AL and BHA significantly lowered the levels of urea nitrogen by 25.25%, 11.65% and 12.81% (P<0.05, F=6.07 to 36.39; FIG. 4A) in the liver and Cr by 11.52%, 8.21% and 12.02% (P<0.05, F=4.808 to 16.31; FIG. 4B) in the serum. The administration of AL and 10 μg BHA dramatically lowered the levels of Cr by 15.28 and 8.14% (P<0.01, F=9.96 to 13.35; FIG. 4B) respectively, in the liver. Data are expressed as mean±S.D. (n=10) and were analyzed via a one-way ANOVA test followed by post-hoc Dunn's multiple comparison tests. ##P<0.01 versus normal control, * P<0.05 and ** P<0.01 versus model control.

The following working examples further illustrate this invention and are not intended to be limiting in any respect.

WORKING EXAMPLES

Example 1A. Preparation of Partially Deacetylated HA

Partially deacetylated HA (DHA) was prepared via hydrazinolysis (see Babasola O., et al., *J Biol Chem* 2014; 289:24779-91). Briefly, 6 g of HA was dissolved in 300 mL of hydrazine monohydrate containing 3 g of hydrazine sulfate. The reaction mixture was incubated in a 65° C. water bath for 72 h. The reaction was quenched in an ice cold water bath and the product was precipitated with cold ethanol. This product was washed twice with cold ethanol and dried under vacuum at room temperature. The sample then was re-dissolved in a mixture of 100 mL of aqueous 5 wt % acetic acid and 60 mL of aqueous 0.5 M iodic acid, and the mixture was kept at 4° C. for 1.5 h. An aqueous 57 wt % $CH_3I$ solution (17.5 mL) was added and the mixture was stirred constantly for another 15 min. The deep violet solution was transferred into a separation funnel, and 150 mL of ethyl ether was used to extract the violet organic component, the aqueous layer containing partially deacetylated HA (DHA) was recovered. The liquid-liquid extraction step was repeated with ethyl ether until complete discoloration was achieved. The pH of the aqueous layer that containing DHA was adjusted to 7.0 with HCl and the DHA was precipitated with cold ethanol, washed with cold ethanol and dried. The product was then dissolved in double-distilled water, dialyzed with 8,000 Da molecular cutoff dialysis tube for 5 days and subsequently lyophilized.

Example 1B. Butylation of DHA

The DHA was reacylated with butyric anhydride to obtain partially butylated HA (BHA) via a preparation method described in a previous paper (see Babasola O, et al. *J Biol Chem* 2014; 289:24779-91). Briefly, 0.1 g of DHA was dissolved in 30 mL of double-distilled water and then 6 mL of saturated sodium bicarbonate solution was added prior to the addition of addition of 6 mL 10% (v/v) butyric anhydride in absolute ethanol. The above reaction mixture was stirred for 1.5 h at room temperature. Subsequently, the reaction was quenched in a boiling water bath for 5 min. The residual ethanol from the reaction mixture was evaporated via rotary evaporation. The BHA sample was dialyzed against double-distilled water with a 8,000 Da molecular weight cutoff dialysis tube for 5 days prior to lyophilization.

Example 1C. $^1H$ NMR Analysis of DHA and BHA

To characterize the structure of DHA and BHA, $^1H$ NMR spectra of 10 mg samples in $D_2O$ were recorded at 348 K using a 500 MHz Bruker Spectrometer. In HA polysaccharide, for each repeating disaccharide unit (-GlcNAc-GlcA-), there are three methyl protons in the GlcNAc, and two anomeric protons in the in GlcNAc and GlcA moieties. The integration ratio of the signals corresponding to the methyl protons to those corresponding to the anomeric proton was 1.5. Based on the $^1H$ NMR spectra of DHA, the integration ratio of the three methyl protons at 2.4-2.5 ppm to the two anomeric protons of GlcNAc and GlcA at 4.9-5.3 ppm was Y. The degree of deacetylation can be calculated according to the equation: Deacetylation (%)=(1.0−(Y/1.5))100). The spectrum of BHA shows additional —$CH_2CH_2CH_3$ proton signals, the ratio of butylation to acetylation in the sample of BHA is the integration ratio of methyl protons in the GlcNAc to the methyl protons in the —$CH_2CH_2CH_3$.

In regard to $^1H$ NMR analysis of HA, DHA and BHA, the data are as follows, HA: δ2.50 (s, —$CH_3$), δ4.40-3.83 (m, other Hs on carbohydrate rings), δ5.09-5.08 (d, anomeric H on GlcNAc of HA), δ4.94-4.93 (d, anomeric H on GlcA of HA). DHA: δ2.50 (s, —$CH_3$), δ4.45-3.84 (m, other Hs on carbohydrate rings), δ5.10- (d, anomeric H on GlcNAc of HA), δ4.95 (d, anomeric H on GlcA of HA), δ5.31 (d, anomeric H on GlcNAc of DHA), δ5.18 (d, anomeric H on GlcA of DHA). BHA: δ2.50 (s, —$CH_3$ of GlcNAc), δ4.40-3.83 (m, other Hs on carbohydrate rings), δ5.10-5.09 (d, anomeric H on GlcNAc of HA), δ4.94-4.93 (d, anomeric H on GlcA of HA), δ5.13 (d, anomeric H on GlcNAc of BHA), δ5.10-5.09 (d, anomeric H on GlcA of BHA), δ2.74 (t, —$CH_2$ of GlcNBu of BHA), δ2.09-2.08 (m, —$CH_2$ of GlcNBu of BHA), δ1.42 (t, —$CH_3$ of GlcNBu of BHA). The GlcNAc-GlcA disaccharide units of HA underwent partial deacetylation, and some of the GlcNAc was converted to GlcN to yield DHA. The anomeric proton corresponding to GlcNAc in the GlcNAc-GlcA unit was observed at 5.09-5.08 ppm as a doublet. The anomeric proton of GlcA in the GlcNAc-GlcA unit was also observed as a doublet at 4.94-4.93 ppm. The newly visible smaller peaks at 5.18-5.31 ppm corresponded to anomeric protons of GlcN-GlcA unit. The anomeric proton of GlcN in the GlcN-GlcA unit was observed at 5.09-5.08 ppm, doublet. The anomeric proton of GlcA in GlcN-GlcA unit was also observed as a doublet at 4.94-4.93 ppm. In the spectrum of DHA, the integration ratio of the three methyl protons to the anomeric protons was calculated to be 1.13. From this ratio, the percentage of deacetylation was calculated to be 24.8%. The spectrum of BHA shows additional —$CH_2CH_2CH_3$ proton signals indicating that a reacylation reaction was occurred and that the ratio of butylation to acetylation was calculated to be 25.4%.

Example 1D. Molecular Weight Estimation of HA, DHA and BHA

The molecular weights of DHA and BHA were estimated by electrophoresis. Briefly, samples were characterized using a 0.75 (w/v) agarose gel in Tris-acetate-EDTA (TAE) buffer, containing 400 mM Tris, 50 mM acetate acid and 9 mM EDTA, pH 8.0. A sample loading buffer was prepared with 0.02 wt % bromophenol blue and 2 M sucrose in TAE buffer. Loading samples were prepared as 15 μL solutions with concentrations of 0.5 mg/mL (HA, DHA, BHA) plus 3 μL loading buffer, then the samples were separating at 100V for ~90 min until the tracking dye migrated to the edge of the gel. After the run, the gel was stained with 0.005% (w/v) Stains-All in 50% (v/v) ethanol, kept in the dark and stained for 48 h. For destaining, the gel was placed in 10% (v/v) ethanol, kept in the dark, destained for 48 h, during which time the destaining solution was replaced three times.

In regard to molecular weight estimation of HA, DHA and BHA, the molecular weight of HA and its derivatives were estimated by agarose gel electrophoresis. The low molecular weight HA ladder includes a molecular mass range of 500-30 kDa was used to estimate the molecular weights of HA, DHA and BHA. The purchased HA had a range of molecular masses from 1800 to 30 kDa, while DHA (DHA1 and DHA2) had a molecular weight of ~60 kDa. The samples of DHA1 and DHA2 were prepared by the same methods but from different batches, indicating that the preparation of 60 kDa DHA via the hydrazinolysis reaction was reproducible. The molecular weight of BHA1 and BHA2 was estimated to be ~30 kDa. They were prepared via the same methods but from the different batches, indicating that the reacylation reaction was also reproducible. AHA was the partial deacetyled HA that was reacylated with acetic anhydride. The molecular weight of AHA was also estimated to be ~30 kDa, suggesting that the reacylation method for preparing different HA-derivatives yielded products with similar molecular weights.

Example 1E. Mass Spectrometry Analysis of HA, DHA and BHA

MS analyses of the samples were performed using a Triple-TOF 5600 mass spectrometer (SCIEX, Concord, Canada) equipped with an electrospray ionization source operated in the negative scanning mode. MS parameters, which were optimized by a 10 μg/mL HA solution via a syringe pump were as follows: Source temperature=550° C.; ion spray voltage=−4500 V; nebulizer gas (N2) pressure=25 psi, heater gas (N2) pressure=50 psi, curtain gas pressure=25 psi, DP=−100 V and CE=−35 eV. Samples at concentrations of 10 μg/mL were injected into the mass spectrometer via a syringe pump to scan for specific fragments corresponding to HA and its derivatives as shown in Table 1 in the TOF-MS scanning mode. Data acquisition was controlled by Analyst 1.6.1 software.

In regard to mass spectrometry analysis of HA, DHA and BHA, following infusion into the Q-TOF MS system via a syringe pump, sample solutions were scanned in the TOF-MS mode. The observed m/z value was very similar to the predicted m/z, as shown in Table 1. Singly charged disaccharides of GlcNAc and GlcA (m/z 396.1160), as well as singly (m/z 775.2257, 797.2076) and doubly charged (m/z 387.1089) tetrasaccharides of GlcNAc and GlcA were observed in the mass spectra of the HA sample. The additional singly charged disaccharide of GlcN and GlcA (m/z 354.1053) observed via TOF-MS spectra showed that the sample of DHA was composed of partially deacetylated HA. The additional singly charged disaccharide of GlcNBu and GlcA (m/z 424.1462) observed in the TOF-MS spectra of BHA showed that the sample contained partially butylated HA. In these specific fragments, singly charged disaccharides of GlcNAc and GlcA (theoretical m/z 396.1142) were the most abundant in all of the samples, and thus this signal was used as the target peak. The relative intensities of the other relevant peaks were calculated based on the target peak as shown in Table 1.

Example 2. Dose Screening on MSU Crystals-Induced Acute Gout in Rats 48 male Wistar rats (8 weeks: 180-200 g), purchased from Yisi Experimental Animal Technology Company Ltd, Jilin, China (SCXK (Ji)-2016-0003), were housed in plastic cages and maintained on a 12-h light/12-h dark cycle (lights on 7:00-19:00 h) under standard laboratory conditions of 55% relative humidity and 23° C.±1° C. They were given standard chow and tap water ad libitum. All experimental procedures were approved by the Animal Ethics Committee of Jilin University (Reference NO. 201605).

An experimental model of MSU-induced gouty arthritis was used in order to evaluate the anti-inflammatory activities of BHA similar as previous studies with some modifications. Rats were randomly divided into eight groups (n=6), including control group (NC), model group (MC), 0.3 mg/kg colchicine group (COL), 5 μg BHA group (5BHA), 10 μg BHA group (10BHA), 25 μg BHA group (25BHA), 50 μg BHA group (50BHA), 100 μg BHA group (100BHA). MSU crystals were suspended in 0.9% sterile saline (30 mg/mL) prior to use. Rats in the colchicine group were orally administered colchicine (0.3 mg/kg) for 8 days. At day 6, MSU solution (100 μL of 30 mg/mL) was intra-articular injected at the right ankles of all rats except the NC group m which were injected with saline solution. 5BHA, 10BHA, 25BHA, 50BHA and 100BHA groups received intra-articular injections of 5, 10, 25, 50, or 100 μg BHA along with MSU solution (100 μL of 30 mg/mL MSU solution contains 5, 10, 25, 50 or 100 μg BHA) were administered according to the stated BHA doses.

The right ankle circumference of all rats at 0, 4, 12, 24 and 48 h after MSU injection was measured. The swelling ratio (%) was used for evaluating the gouty arthritis and calculated according to the change of the circumference following the formula: Swelling ratio (%)=($C_t$−$C_0$)/$C_0$. Wherein, $C_t$ represented the circumference at t hour and $C_0$ represented the circumference at 0 hour. MSU injection significantly increased the swelling ratio of the right ankle in rats at 12, 24 and 48 hours after MSU injection separately (P<0.01, F=12.09 to 28.24) compared with control rats. Treatment with 0.3 mg/kg COL significantly suppressed swelling of the ankle ($P<0.05$, F=6.79) compared to MSU treated group at 4 h only. Treatment with BHA significantly suppressed swelling at 4 h ($P<0.05$, F=4.89 to 8.32), and 12 h ($P<0.05$, F=5.33 to 15.70). At doses of 10 μg, 50 μg and 100 μg, BHA showed significant suppressing of swelling effect at 48 h ($P<0.05$, F=4.97 to 7.29) compared to the MSU treated group.

Example 3A. Protocol for Inducing Acute Gout in Rats by MSU Crystals Injection and Treatment by BHA Male Wistar rats (n=50, 8 weeks: 160-200 g) were purchased from Liaoning Changsheng Biotechnology Company Ltd, Jilin, China (SCXK (Liao)-2015-0001). These rats were housed in plastic cages and maintained on a 12-h light/12-h dark cycle (lights on 7:00-19:00 h) under standard laboratory conditions of 55% relative humidity and at 23° C.±1° C. They were given standard chow (Liaoning Changsheng Biotechnology Company Ltd, Jilin, China) and tap water ad libitum. All experimental procedures were approved by the Animal Ethics Committee of Jilin University (Reference NO. 201605).

An experimental model of MSU-induced gouty arthritis was used in order to evaluate the anti-inflammatory activities of BHA. Rats were randomly divided into five groups (n=10), include a control group (NC), a model group (MC), a 0.3 mg/kg colchicine group (COL), a 10 μg BHA group (10BHA) and a 50 μg BHA group (50BHA). MSU crystals were suspended in 0.9% sterile saline (30 mg/mL) prior to use. The colchicine group rats were orally administrated colchicine (0.3 mg/kg) for 8 days, and all rats except for the control group were injected with 3 mg of MSU (Sigma, USA) at the $6^{th}$ day into the right ankle synovial space 1 h after gavage feeding. Meanwhile a turbid sample of MSU mixed with 100 μg of BHA or 500 μg of BHA per mL of solution for 10BHA rats or 50BHA rats. At the $8^{th}$ day, 1 h after the administration of the final agents, blood was sampled from the caudal veins of the rats and the right ankle joints of the rats were collected and fixed in 4% paraformaldehyde. Serum was separated and stored at −80° C. prior to analysis (FIG. 2A, E).

The right ankle circumferences of all rats at 0, 4, 12, 24 and 48 h after MSU injection were measured. The swelling ratio (%) was used to evaluate the gouty arthritis and calculated according to the change of the circumference via the formula: Swelling ratio (%)=$(C_t-C_0)/C_0$, wherein, $C_t$ represented the circumference at time t (in h) and $C_0$ represented the circumference at 0 h.

At 48 h post-MSU crustal injection, X-ray image of right ankle bones were recorded with Multi Mode Small Animal Living Imaging System (Kodak, USA) to evaluate the bone injury of each rat's ankle.

The right ankles of rats were collected and fixed in 4% paraformaldehyde, and subsequently decalcified using 10% ethylenediaminetetraacetic acid. They were then dehydrated by processing in alcohol/xylene mixtures with different proportions and concentrations. The histological sections were later stained with hematoxylin and eosin for observation under an optical microscope (200×). The histopathological changes were analyzed with regard to deformaties of the joint synovium and infiltration by inflammatory cells into the ankle.

The serum levels of interleukin-1α (IL-1α, 41734), IL-1β (43360), interleukin-6 (IL-6, 41731), interleukin-8 (IL-8, 41716), IL-10 (41736), interleukin-16 (IL-16, 41628), C—X—C motif chemokine 10 (CXCL10, 41570), monocyte chemoattractant protein 1 (MCP-1, 41640), macrophage inflammatory protein 1α (MIP-1α, 41645), interferon gamma (IFN-γ, 41739), TNF-α (41721), tumor necrosis factor-β (TNF-β, 41673), nuclear factor κ-light-chain-enhancer of activated B cells (NF-κB, 43358), 6-keto-prostaglandin F-1α (6-Keto-PGF1α, 41809) and prostaglandin E2 (PGE2, 41609) in rats were determined by the ELISA method using related Elisa Kits (Yuanye Bio-Technology Co. Ltd, Shanghai, China) according to the manufacturer's instructions.

Example 3B. Experiments on OXO-Induced Hyperuricemia in Mice and Treatment by BHA Male Balb/C mice (n=50, 8 weeks: 18-22 g), purchased from Yisi Experimental Animal Technology Company Ltd, Jilin, China (SCXK (Ji)-2016-0003). These mice were housed in plastic cages and maintained on a 12-h light/12-h dark cycle (lights on 7:00-19:00 h) under standard laboratory conditions of 55% relative humidity and 23±1° C. They were given standard feed and tap water ad libitum. All experimental procedures were approved by the Animal Ethics Committee of Jilin University (Reference NO. 201605).

Due to the presence of uricase in mice, a hyperuricemic mouse model was established by using uricase inhibitor and large amounts of purine. Mice were randomly divided into five groups (n=10), including the control group (NC), model group (MC), 20 mg/kg of AL (Shimao Tianjie Pharmaceutical Co. Ltd, Jiangsu, China) group, 10 μg BHA group (10BHA) and 50 μg BHA group (50BHA). Oral administration of AL and intraperitoneal injection of BHA were administered according to the required dose, and all mice were gavage fed 20 g/kg yeast extract powder 12 h prior to the administration of AL and BHA except for NC mice for 8 days. From the $6^{th}$ to $8^{th}$ day, 1-h prior to AL and BHA administration, 300 mg/kg of OXO (Sigma, USA) was intraperitoneally injected to all of the mice except those in the control group. At 1 h after the final drug administration, blood was sampled from caudal veins of the mice, serum was separated and their livers were quickly collected (FIG. 3A, E). All samples were stored at −80° C. until assay measurements were performed.

The serum UA concentrations and XO levels in the serum and liver were determined with a standard diagnostic kit (MAK077, MAK078 Sigma, USA) according to the manufacturer's instructions.

The levels of reactive oxygen species (ROS, 43355), malondialdehyde (MDA, 43124) glutathione peroxidase (GSH-Px, 43390), superoxide dismutase (SOD, 43125), catalase (CAT, 43356), creatinine (Cr, 43353) and blood urea nitrogen (BUN, 43352) in the serum and livers of mice were determined using ELISA Kits (Yuanye Bio-Technology Co. Ltd, Shanghai, China) according to the manufacturer's instructions.

Example 4. Statistical Analysis

All results collected in vivo were expressed as mean±S.D. One-way analysis of variance (ANOVA) was used to evaluate statistical significance of the data, and this was followed by post-hoc Dunn's multiple comparisons test by SPSS 19.0 Software (IBM corporation, Armonk, USA). P values <0.05 were considered to be statistically significant.

It will be understood by those skilled in the art that this description is made with reference to certain embodiments and that it is possible to make other embodiments employing the principles of the invention which fall within its scope as defined by the claims.

We claim:
1. A method for treating of a condition or disease selected from the group consisting of uric acid nephropathy, and uric acid renal stones, comprising administering to a patient in need thereof a therapeutically effective amount of a

TABLE 1

The theoretical and observed molecular ion species in HA and HA derivatives along with their relative intensities.

| Molecular ions | Charge | Theoretical m/z | Observed m/z HA | Observed m/z DHA | Observed m/z BHA |
|---|---|---|---|---|---|
| Disaccharide of GlcNAc and GlcA | −1 | 396.1142 | 396.1160 (100%) | 396.1138 (100%) | 396.1139 (100%) |
| Tetrasaccharide of GlcNAc and GlcA | −1 | 775.2257 | 775.2299 (20.0%) | 775.2268 (23.3%) | 775.2309 (15.7%) |
| Tetrasaccharide of GlcNAc and GlcA | −1 | 797.2076 | 797.2069 (13.7%) | 797.2144 (5.5%) | 797.2206 (10.8%) |
| Tetrasaccharide of GlcNAc and GlcA | −2 | 387.1089 | 387.1100 (8.0%) | 387.1078 (12.0%) | 387.1107 (7.2%) |
| Disaccharide of GlcN and GlcA | −1 | 354.1036 | | 354.1053 (23.3%) | |
| Disaccharide of GlcNBu and GlcA | −1 | 424.1455 | | | 424.1462 (27.0%) |

TABLE 2

The effects of COL and BHA on the inflammation factors in in rats with MSU-induced acute gout.

| | NC | MC | COL | 10BHA | 50BHA |
|---|---|---|---|---|---|
| IL-1α (pg/mL) | 79.4 ± 5.4 | 72.2 ± 7 | 74.3 ± 12.6 | 71.5 ± 11.2 | 77.4 ± 13 |
| IL-1β (pg/mL) | 19.6 ± 0.5 | 19.9 ± 0.5 | 19.1 ± 1.2 | 19.6 ± 1.6 | 18.8 ± 0.8 * |
| IL-6 (pg/mL) | 71.1 ± 4.7 | 74.2 ± 6.2 | 74.7 ± 7.9 | 78.5 ± 5.6 | 75 ± 5.3 |
| IL-8 (pg/mL) | 232 ± 10.7 | 231.8 ± 8.6 | 222.7 ± 11.5 | 213.8 ± 11.4 | 216.6 ± 11.6 |
| IL-10 (pg/mL) | 11.8 ± 0.6 | 11 ± 0.8 # | 11.5 ± 0.7 | 12 ± 0.9 * | 11.6 ± 1.1 |
| IL-16 (pg/mL) | 397.9 ± 31. | 405.7 ± 20.5 | 416.7 ± 16.1 | 399.3 ± 14.8 | 401.2 ± 25.1 |
| IP-10 (pg/mL) | 143.8 ± 7.7 | 158.4 ± 23.4 | 153.5 ± 20.3 | 154.3 ± 18 | 150.5 ± 7.5 |
| MCP-1 (pg/mL) | 320.2 ± 16 | 345.8 ± 24.2 | 311.5 ± 20.8 | 321.2 ± 20.5 | 292 ± 27.8 ** |
| MIP-1α (pg/mL) | 289.8 ± 25. | 289.2 ± 20.3 | 294.6 ± 21.5 | 282.8 ± 23.6 | 283.9 ± 12.7 |
| IFN-γ (pg/mL) | 99.6 ± 26 | 112.8 ± 21.6 | 88.2 ± 35 | 107.4 ± 7.6 | 75.4 ± 31.7 * |
| TNF-α (pg/mL) | 154.6 ± 13. | 156.2 ± 13 | 154.8 ± 8.5 | 155.9 ± 11.4 | 152.7 ± 12.1 |
| TNF-β (pg/mL) | 121.4 ± 28. | 127.7 ± 22.8 | 124.8 ± 10.5 | 139.1 ± 25.7 | 129 ± 21.9 |
| NF-κB (pg/mL) | 358.1 ± 97 | 501.3 ± 102.9 | 494.6 ± 132. | 589.8 ± 104. | 513 ± 74.1 |
| 6-Keto-PGF1α | 214.5 ± 17. | 251.3 ± 21.7 | 266.3 ± 12.7 | 257 ± 20.8 | 262 ± 10.8 |
| PGE2 (pg/mL) | 195 ± 10.5 | 199.5 ± 8.6 | 207.7 ± 10 | 209.7 ± 17.3 | 193.2 ± 12.7 |

Data are expressed as mean ± S.D.
(n = 10) and analyzed via a one-way ANOVA test followed by post-hoc Dunn's multiple comparison tests.
$P < 0.05$ versus control rats,
* $P < 0.05$ and
** $P < 0.01$ versus model rats.

TABLE 3

The effects of AL and BHA on the factors related to oxidative stress and renal function in hyperuricemia mice.

| | | NC | MC | AL | 10BHA | 50BHA |
|---|---|---|---|---|---|---|
| Serum | ROS (U/mL) | 252.2 ± 24.1 | 266.1 ± 15.8 | 240.9 ± 23.9 * | 226.6 ± 17.9 *** | 227.2 ± 17.9 *** |
| | SOD (U/mL) | 171 ± 10.6 | 157.6 ± 7.3 # | 159.2 ± 8 | 166.6 ± 11.8 | 161.2 ± 8 |
| | GSH-PX (U/mL) | 234.4 ± 10.1 | 238.8 ± 12.1 | 231.8 ± 7.7 | 246.8 ± 10.2 | 231.4 ± 13.3 |
| | CAT (U/mL) | 44.4 ± 6 | 41.1 ± 4.3 | 41.6 ± 5.6 | 43.3 ± 4.6 | 41.5 ± 6 |
| | MDA (nmol/mL) | 10.4 ± 0.8 | 10.9 ± 0.7 | 10.2 ± 0.5 * | 10.4 ± 0.5 | 10.5 ± 0.3 |
| Liver | ROS (U/mg) | 67.1 ± 5.9 | 77.0 ± 3.6 ## | 63.2 ± 6.2 *** | 70.8 ± 3.7 ** | 69.6 ± 7.1 * |
| | SOD (U/mg) | 46.5 ± 2.6 | 50.4 ± 0.8 | 48.5 ± 3.4 | 56.8 ± 5.8 * | 57.2 ± 4.4 ** |
| | GSH-PX (U/mg) | 71.2 ± 7.1 | 73.9 ± 6.9 | 66.1 ± 7.2 | 78.8 ± 8 | 77.9 ± 7.3 |
| | CAT (U/mg) | 13.2 ± 1.6 | 12.7 ± 1.6 | 12.9 ± 1.3 | 13.1 ± 1.4 | 14.1 ± 1.5 |
| | MDA (nmol/mg) | 3.2 ± 0.3 | 3.5 ± 0.2 # | 3.1 ± 0.2 ** | 3.4 ± 0.2 | 3.5 ± 0.2 |

Data are expressed as mean ± S.D.
(n = 10) and analyzed via a one-way ANOVA test followed by post-hoc Dunn's multiple comparison tests.
$P < 0.05$ and
$P < 0.01$ versus control mice,
* $P < 0.05$,
** $P < 0.01$ and
*** $P < 0.001$ versus model mice.

hyaluronic acid derivative comprising repeating units of a disaccharide of Formula (I), wherein a portion of the disaccharide units of Formula(I) have been independently replaced with a disaccharide structure of Formula (II) wherein R is —C(O)—(C$_2$-C$_4$)-alkyl, or a pharmaceutically acceptable sodium- or potassium-salt, ester, or glucoside thereof,

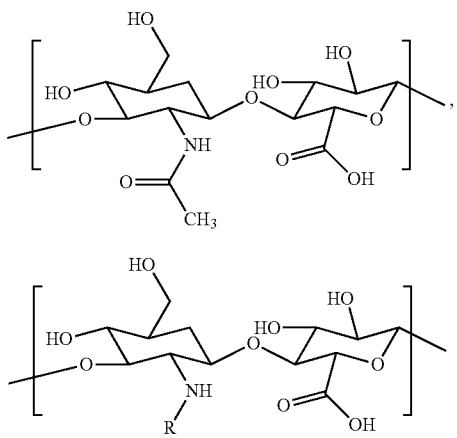

wherein the hyaluronic acid derivative has a molecular weight of at least about 20 kDa.

2. A method of modulating of creatinine levels, urea nitrogen, and/or uric acid levels, comprising administering to a patient in need thereof a therapeutically effective amount of a hyaluronic acid derivative comprising repeating units of a disaccharide of Formula (I), wherein a portion of the disaccharide units of Formula (I) have been independently replaced with a disaccharide structure of Formula (II) wherein R is —C(O)—(C$_2$-C$_4$)-alkyl, or a pharmaceutically acceptable sodium- or potassium-salt, ester, or glucoside thereof,

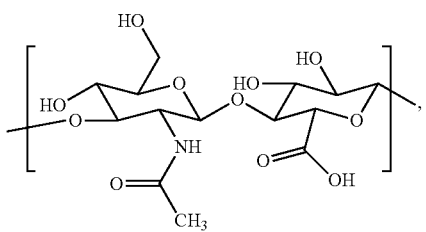

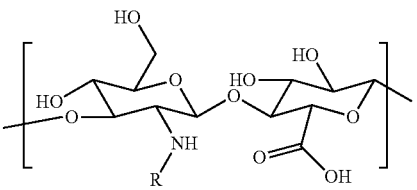

wherein the hyaluronic acid derivative has a molecular weight of at least about 20 kDa, wherein the modulating of creatinine levels prevents rejection of a donor organ.

3. The method of claim 1, wherein the inflammation results from the production of pro-inflammatory cytokines in the patient.

4. The method of claim 1, wherein the hyaluronic acid derivative is cross-linked.

5. The method of claim 1, wherein R is —C(O)—(C$_3$)-alkyl.

6. The method of claim 1, wherein the portion of N-acetyl groups which are replaced is at least about 10%.

7. The method of claim 1, wherein the portion of N-acetyl groups which are replaced is between about 20% to about 80%.

8. The method of claim 1, wherein the molecular weight is at least about 30 kDa.

9. The method of claim 1, wherein the molecular weight is between about 20 kDa to about 250 kDa.

10. The method of claim 2, wherein the inflammation results from the production of pro-inflammatory cytokines in the patient.

11. The method of claim 2, wherein the hyaluronic acid derivative is cross-linked.

12. The method of claim 2, wherein R is —C(O)—(C$_3$)-alkyl.

13. The method of claim 2, wherein the portion of N-acetyl groups which are replaced is at least about 10%.

14. The method of claim 2, wherein the portion of N-acetyl groups which are replaced is between about 20% to about 80%.

15. The method of claim 2, wherein the molecular weight is at least about 30 kDa.

16. The method of claim 2, wherein the molecular weight is between about 20 kDa to about 250 kDa.

17. The method of claim 2, wherein the donor organ is a liver.

18. The method of claim 2, wherein the donor organ is a kidney.

* * * * *